United States Patent
Lu (10) Patent No.: US 12,026,879 B2
(45) Date of Patent: Jul. 2, 2024

(54) METHOD FOR DETECTING THE PRESENCE OF PNEUMONIA AREA IN MEDICAL IMAGES OF PATIENTS, DETECTING SYSTEM, AND ELECTRONIC DEVICE EMPLOYING METHOD

(71) Applicant: Fulian Precision Electronics (Tianjin) Co., LTD., Tianjin (CN)

(72) Inventor: Meng-Ping Lu, New Taipei (TW)

(73) Assignee: Fulian Precision Electronics (Tianjin) Co., LTD., Tianjin (CN)

( * ) Notice: Subject to any disclaimer, the term of this patent is extended or adjusted under 35 U.S.C. 154(b) by 382 days.

(21) Appl. No.: 17/536,284

(22) Filed: Nov. 29, 2021

(65) Prior Publication Data

US 2022/0405916 A1 Dec. 22, 2022

(30) Foreign Application Priority Data

Jun. 18, 2021 (CN) .......................... 202110680989.5

(51) Int. Cl.
G06T 7/00 (2017.01)
A61B 5/08 (2006.01)
G06V 10/25 (2022.01)
G06V 10/40 (2022.01)
G06V 10/776 (2022.01)

(52) U.S. Cl.
CPC ............. *G06T 7/0012* (2013.01); *A61B 5/08* (2013.01); *G06V 10/25* (2022.01); *G06V 10/40* (2022.01); *G06V 10/776* (2022.01); *G06V 2201/03* (2022.01)

(58) Field of Classification Search
CPC .......... G06T 7/0012; G06T 7/70; A61B 5/08; G06V 10/25; G06V 10/40; G06V 10/776; G06V 2201/03
See application file for complete search history.

(56) References Cited

U.S. PATENT DOCUMENTS 10,691,980 B1 * 6/2020 Guendel ................. G06T 7/70
2020/0134825 A1 * 4/2020 Li ........................ G06N 3/045
(Continued)

OTHER PUBLICATIONS

Khoiriyah et al. "Convolutional Neural Network for Automatic Pneumonia Detection in Chest Radiography" <https://ieeexplore.ieee.org/document/9231540> (Year: 2020).*
(Continued)

*Primary Examiner* — Ming Y Hon
(74) *Attorney, Agent, or Firm* — ScienBiziP, P.C.

(57) ABSTRACT

A pneumonia area detecting system includes an information obtaining module, an image preprocessing module, a calculating module, and a pneumonia area detecting model. The information obtaining module obtains medical images and a frame size of an initial pneumonia area. The image preprocessing module processes the medical images to obtain a standard format image. The calculating module processes the frame size of the initial pneumonia area through a preset algorithm and the standard format image, to obtain a frame size of a standard format pneumonia area. The pneumonia area detecting model obtains an output pneumonia area according to the standard format image and the frame size of the standard format pneumonia area. A pneumonia area detecting method and an electronic device are also provided in the present disclosure.

15 Claims, 4 Drawing Sheets

(56) References Cited

U.S. PATENT DOCUMENTS

| | | | | |
|---|---|---|---|---|
| 2020/0388395 | A1* | 12/2020 | Umezawa | G06N 7/01 |
| 2021/0327071 | A1* | 10/2021 | Vartakavi | G06N 3/08 |
| 2021/0350235 | A1* | 11/2021 | Levi | G06N 3/08 |
| 2021/0361897 | A1* | 11/2021 | Neal | A61B 5/1071 |
| 2021/0383534 | A1* | 12/2021 | Tadross | G06V 10/764 |
| 2022/0092788 | A1* | 3/2022 | Wang | G06N 3/045 |
| 2022/0301156 | A1* | 9/2022 | Fang | G06N 3/0895 |
| 2022/0309655 | A1* | 9/2022 | Teshigawara | G16H 30/40 |
| 2022/0366680 | A1* | 11/2022 | Rasolzadeh | G16H 30/40 |
| 2023/0038364 | A1* | 2/2023 | Bhowmick | G06N 3/045 |

OTHER PUBLICATIONS

Manuel Vazquez Enriquez; A Deep Learning Approach for Pneumonia Detection On Chest X-Ray; 2019; 23-58 Pages.

Zhang, Xudong, et al; FPAENet: Pneumonia Detection Network Based on Feature Pyramid Attention Enhancement; Nov. 16, 2020.

* cited by examiner

METHOD FOR DETECTING THE PRESENCE OF PNEUMONIA AREA IN MEDICAL IMAGES OF PATIENTS, DETECTING SYSTEM, AND ELECTRONIC DEVICE EMPLOYING METHOD

TECHNICAL FIELD

The present disclosure relates to human health, particularly to detecting an area of a human patient indicating the presence of disease.

BACKGROUND

Medical imaging technology has become an indispensable means in modern medical diagnosis and treatment. Medical imaging is an important means to detect pneumonia. However, the characteristics of pneumonia in medical images are not obvious, and diagnosis of the disease is difficult based on medical images alone.

Image target detection technology is often used to assist recognition of certain conditions. However, the accurate detection of pneumonia in human patients is low.

Therefore, improvement is desired.

DETAILED DESCRIPTION

The technical solutions in the embodiments of the present disclosure will be described in conjunction with the accompanying drawings in the embodiments of the present disclosure. Obviously, the described embodiments are part of the embodiments of the present disclosure, not all of them. Based on the embodiments of the present disclosure, all other embodiments obtained by those of ordinary skill in the art without creative work shall fall within the protection scope of the present disclosure.

It should be noted that "at least one" in the embodiment of the present disclosure refers to one or more, and multiple refers to two or more. Unless otherwise defined, all technical and scientific terms used herein have the same meanings as those generally understood by those skilled in the technical field in the present disclosure. The terms used in the description of the present disclosure are only for the purpose of describing specific embodiments and are not intended to limit the present disclosure.

It should be noted that in the embodiment of the present disclosure, "first", "second" and other words are only used for the purpose of distinguishing description, and cannot be understood as indicating or implying relative importance, nor as indicating or implying order. The features defining "first" and "second" may explicitly or implicitly include one or more of the features. In the description of the embodiments of the present disclosure, the words "exemplary" or "for example" are used as examples, examples or explanations. Any embodiment or design described as "exemplary" or "for example" in the embodiments of the present disclosure shall not be interpreted as being more preferred or advantageous than other embodiments or designs. Specifically, the use of the words "exemplary" or "for example" is not intended to present the relevant concepts in a specific way.

The characteristics of pneumonia in medical images are not obvious, and it is difficult to diagnose the disease based on medical images alone.

An embodiment of the present disclosure provides a method for detecting the likely presence of pneumonia and a detecting system which can accurately identify the portions of the human body exhibiting the characteristics of pneumonia by confirming the anchor point and the size of pneumonia area in the image, thus reducing the workload of later identification.

Some embodiments of the present disclosure are described in detail below in combination with the accompanying drawings. The following embodiments and features in the embodiments may be combined with each other without conflict.

Figure 1:
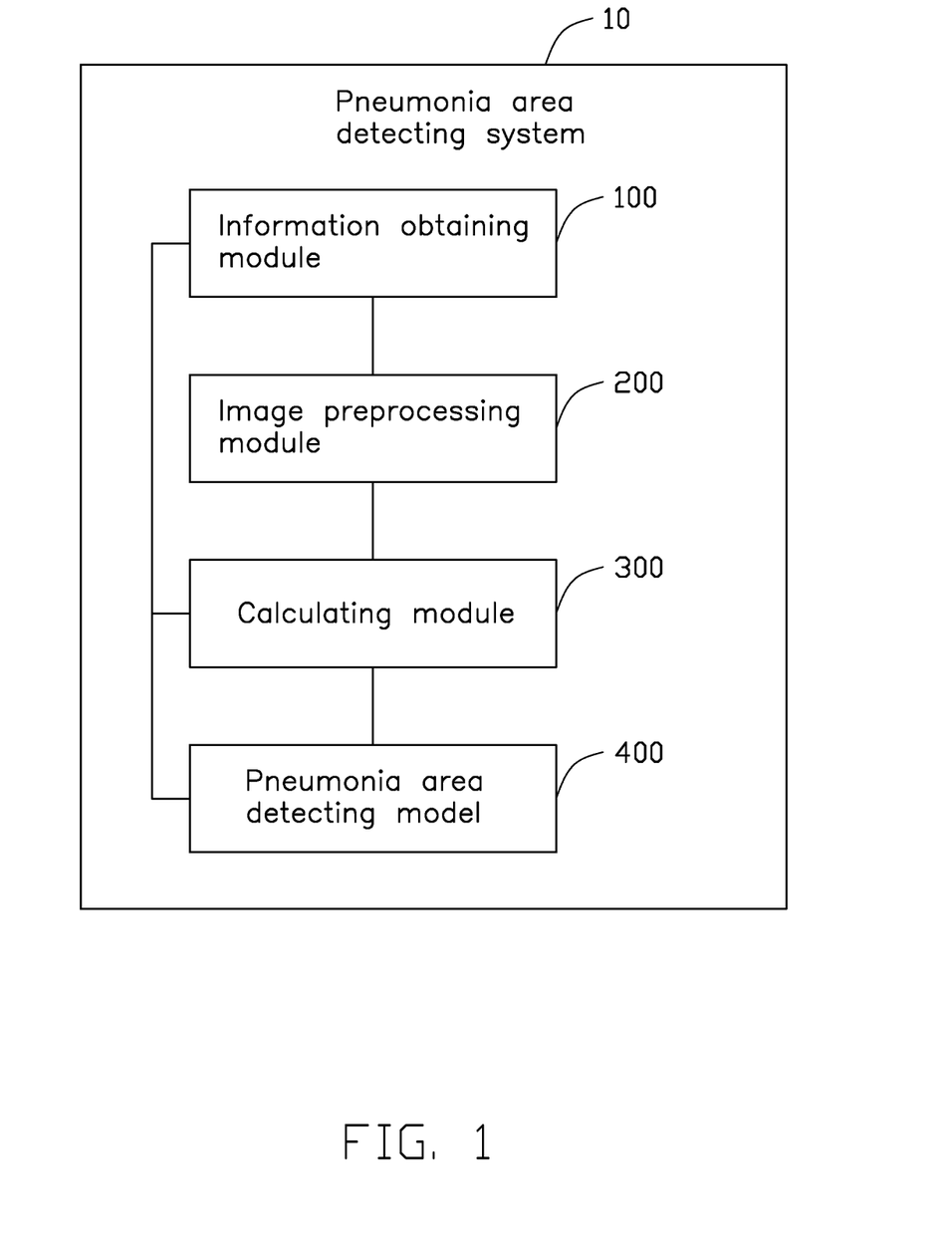
FIG. 1 is a schematic diagram of a pneumonia area detecting system according to an embodiment of the present disclosure.

FIG. 1 is a schematic diagram of a pneumonia area detecting system 10 according to an embodiment of the present disclosure.

The pneumonia area detecting system 10 includes an information obtaining module 100, an image preprocessing module 200, a calculating module 300, and a pneumonia area detecting model 400. The image preprocessing module 200 is connected to the information obtaining module 100, the calculating module 300 is connected to the image preprocessing module 200 and the information obtaining module 100, and the pneumonia area detecting model 400 is connected to the information obtaining module 100 and the calculating module 300.

In one embodiment, the information obtaining module 100 is used to acquire a medical image to be processed. The medical images to be processed can include, but are not limited to, X-ray film, computed tomography (CT) images, magnetic resonance (MR) images, ultrasound images, and nuclear medicine images.

The information obtaining module 100 is also used to obtain the bounding box size of an initial pneumonia area. The frame size of the initial pneumonia area can be set according to the image size of the medical image to be processed. It can be understood that the frame size of the initial pneumonia area is smaller than the image size of the medical image to be processed.

In the embodiment, the image preprocessing module 200 is used to process the medical image to be processed through a preset image preprocessing method, to obtain a standard format image. It can be understood that the preset image preprocessing method includes calculating an average value of sizes and a standard deviation of the medical images to be processed, and outputting standard format images in batches according to the average value of sizes and the standard deviation of the medical image to be processed. The average value of sizes is an average image size of the medical images to be processed, and the standard deviation is a standard deviation between the size of each medical image to be processed and the average image size. In the embodiment of the present disclosure, firstly, the size of the medical image to be processed is uniformly adjusted to the average image size according to the average image size and the standard deviation of the medical image to be processed, and then the medical image to be processed is scaled according to the ratio between the average image size and the size corresponding to the standard image format, so as to obtain the medical image in a standard format in batch (i.e. a standard format image). In one embodiment, the format of the standard format image can be pneumonia area detecting system 1024×pneumonia area detecting system 1024 pixels.

In the embodiment, the calculating module 300 is used to process the frame size of the initial pneumonia area according to the standard format image, to obtain the frame size of a pneumonia area in the standard format. The calculating module 300 may use a k-means clustering algorithm or other similar algorithms, which are not specifically limited here. For example, K-means is an unsupervised partition clustering algorithm. When the calculating module 300 uses the K-means clustering algorithm, the K-means calculation can be used to calculate and filter the frame size of the pneumonia area suitable for the size of the standard format image according to the frame size of the initial pneumonia area.

In the embodiment, the frame size of the pneumonia area can be calculated by multiplying an anchor size of the pneumonia area by a scaling scale. A pneumonia area anchor is an image region that can be used to determine the pneumonia area in the medical image to be processed. Since the sizes of the medical images to be processed may be different, when calculating the frame size of the pneumonia area, it is necessary to multiply the pneumonia area anchor by the scaling scale, to convert the size of the pneumonia area anchor under the standard format image.

The shape of the pneumonia area anchor can be geometric, such as a rectangle, circle, ellipse, or it can be irregular.

The pneumonia area detecting model 400 is used to output a pneumonia area according to the standard format image and the frame size of the pneumonia area.

It is understandable that the pneumonia area detecting model 400 may be an EfficientDet pneumonia area detection model. EfficientNet is a convolutional neural network with a single-stage detection framework. EfficientNet enlarges the network from three dimensions of depth, width, and resolution by using a composite coefficient through a new model scaling method, and then obtains a better set of composite coefficients based on neural structure search technology, including wider, deeper, and higher resolution.

It can be understood that EfficientDet is built on EfficientNet, which scales the model of EfficientNet network, and optimizes the detection of pneumonia area by combining the bidirectional feature pyramid network (BiFPN). Efficientdet model can be divided into EfficientDet D1 to EfficientDet D7 according to calculation speed and accuracy. With the increase of model number, the calculation speed gradually slows down, but the accuracy also gradually improves. For example, compared with EfficientDet D1, the calculation speed of EfficientDet D7 gradually slows down, but the accuracy also gradually improves. It can be understood that the EfficientDet D4 model is used in the embodiment of the application to take into account or balance the calculation speed and accuracy of EfficientDet.

It can be understood that in the previous feature pyramid neural network, feature fusion is fused by simple addition, which means that the weighting of each feature graph is equal. Different features have different contributions to the results. Therefore, a learnable decay of weighting is introduced into the BiFPN layer. The weighting decay is calculated together with the overall weight through the AdamW learning efficiency optimizer to learn the importance of different input features. At the same time, the top-down and bottom-up multi-scale feature fusion are repeatedly applied. The pneumonia area detecting model 400 can also use the AdamW learning efficiency optimizer to improve the convergence of the pneumonia area detecting model 400. In the embodiment, the weighting decay can be set to 0.1.

In the embodiment, the pneumonia area detecting model 400 is also used to distinguish the background and the pneumonia area in the standard format image using a focal loss function. It is understandable that the learning efficiency of the pneumonia area detecting system 10 can be improved by using the focal loss function.

In the embodiment, if there is no pneumonia area in the standard format image, the pneumonia area detecting system 10 can directly output the standard format image.

Figure 2:
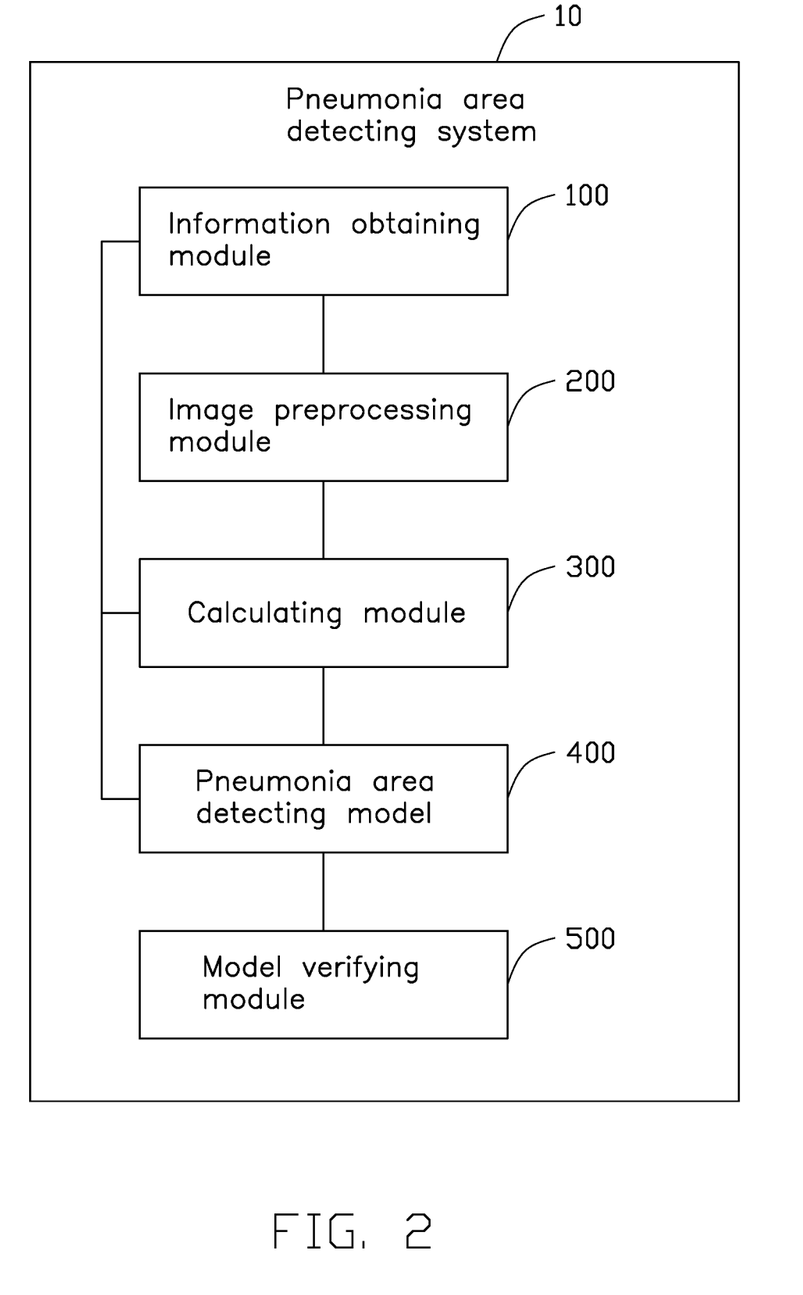
FIG. 2 is a schematic diagram of the pneumonia area detecting system according to another embodiment of the present disclosure.

FIG. 2 is a schematic diagram of the pneumonia area detecting system 10 according to another embodiment of the present disclosure.

The difference from the pneumonia area detecting system 10 shown in FIG. 1 is that the pneumonia area detecting system 10 shown in FIG. 2 further includes a model verifying module 500.

In the embodiment, the model verifying module 500 is connected to the pneumonia area detecting model 400. The model verifying module 500 is used to obtain a standard pneumonia area and verify the intersection over union (IOU) between an output pneumonia area and the standard pneumonia area. If the IOU between the output pneumonia area and the standard pneumonia area is greater than a preset value (such as 0.5), the output pneumonia area is output, and the output pneumonia area is recorded as a true value. If the IOU between the output pneumonia area and the standard pneumonia area is less than the preset value, the output pneumonia area is not output and the output pneumonia area is recorded as a false value.

In the embodiment, a recall rate can be used to calculate the IOU between a pneumonia area output by the pneumonia area detecting system 10 and the standard pneumonia area to verify whether the output of the pneumonia area detecting model 400 meets training requirements.

It is understandable that when calculating the recall rate which is to be used, the value of IOU ranging from 0.5 to 0.95 can be filtered and calculated in steps of 0.05. The recall rate can be calculated by formula (1).

$$\text{mAP} = \Sigma_{th} = \{0.5, 0.55, \ldots, 0.95\} \text{AP}(\text{IOU}_{th} = \text{th})/10 \quad (1)$$

The mAP is the recall rate, and the parameter AP ($\text{IOU}_{th}$=th) is a IOU threshold.

In the embodiment, the sensitivity can also be used to verify whether the pneumonia area detecting system 10 can correctly detect the presence or non-presence of a pneumonia area in the standard format image.

In the embodiment, the pneumonia area detecting model 400 is also used to determine whether to continue training according to the parameters such as mAP and sensitivity output by the model verifying module 500.

It can be understood that when image target detection is carried out, image flipping and translation are often used to expand a training set. While image flipping and translation will increase the network resources required for model training, the effect on pneumonia area recognition is limited. Therefore, when the pneumonia area detecting system 10 trains in the pneumonia area detecting model 400, it can accurately identify the pneumonia area by selecting the appropriate pneumonia area anchor point and size rather than by increasing the training set.

When the pneumonia area detecting model 400 is trained, the learning rate decay of the pneumonia area detecting model 400 can be set to 1000 (decay once per 1000 iterations), the number of samples selected for a single training can be set to 8, and the number of training times of all samples can be set in the calculating module 300. When the pneumonia area detecting model 400 sets the parameters as described above, the mAP of the pneumonia area output by the pneumonia area detecting model 400 is 54.3% and the sensitivity is 63%. That is, it can accurately identify the pneumonia area and reduce the workload of later identification.

In the embodiment, the pneumonia area detecting system 10 can normalize medical images of different specifications according to the K-means clustering algorithm to obtain medical images in a standard format. The information obtaining module 100 can input the medical image in the standard format into the EfficientDet model to determine the presence or non-presence of a pneumonia area in the medical image. It can be understood that since the medical image input into the EfficientDet model has been normalized, the EfficientDet model does not need to process the image specification, but only needs to select the anchor point and frame of the pneumonia area, which improves the detection efficiency of the pneumonia area detecting system 10 and reduces the demand for computing resources during calculation.

Figure 3:
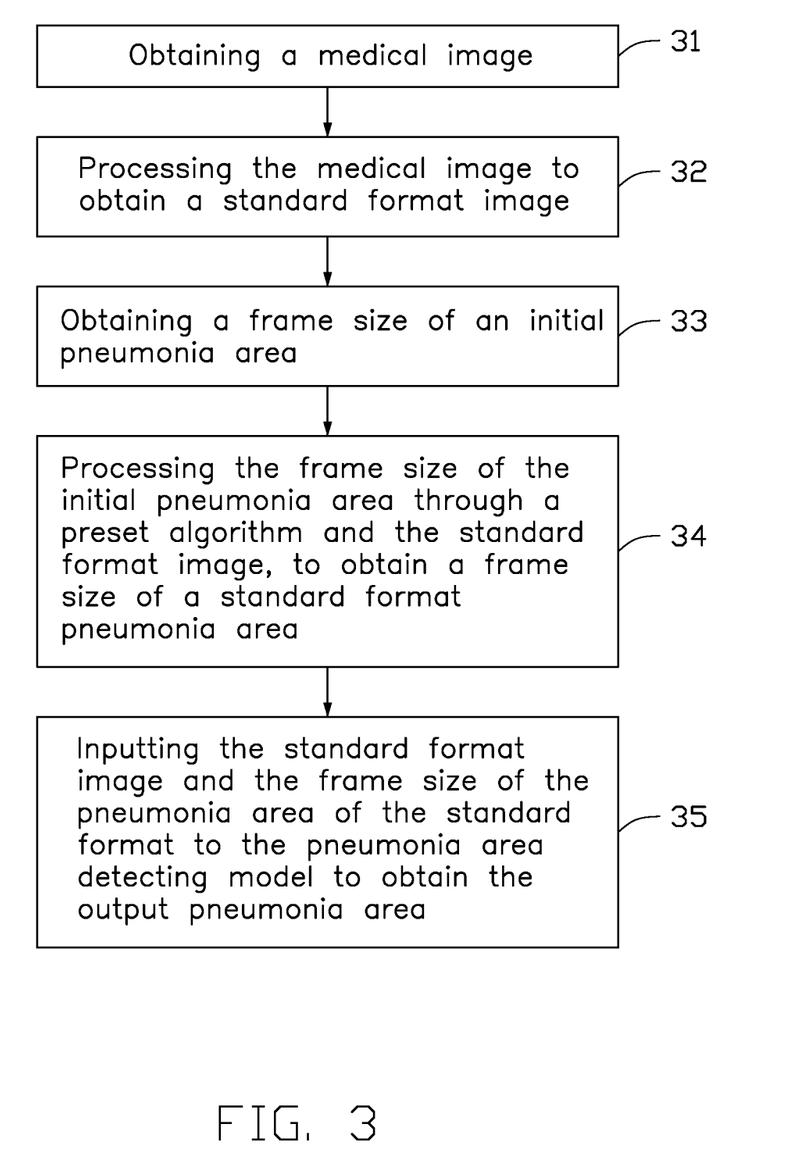
FIG. 3 is a schematic diagram of a pneumonia area detecting method according to an embodiment of the present disclosure.

FIG. 3 is a flowchart depicting an embodiment of a pneumonia area detecting method. The pneumonia area detecting method is applied to the pneumonia area detecting system 10. The method is provided by way of example, as there are a variety of ways to carry out the method.

Figure 4:
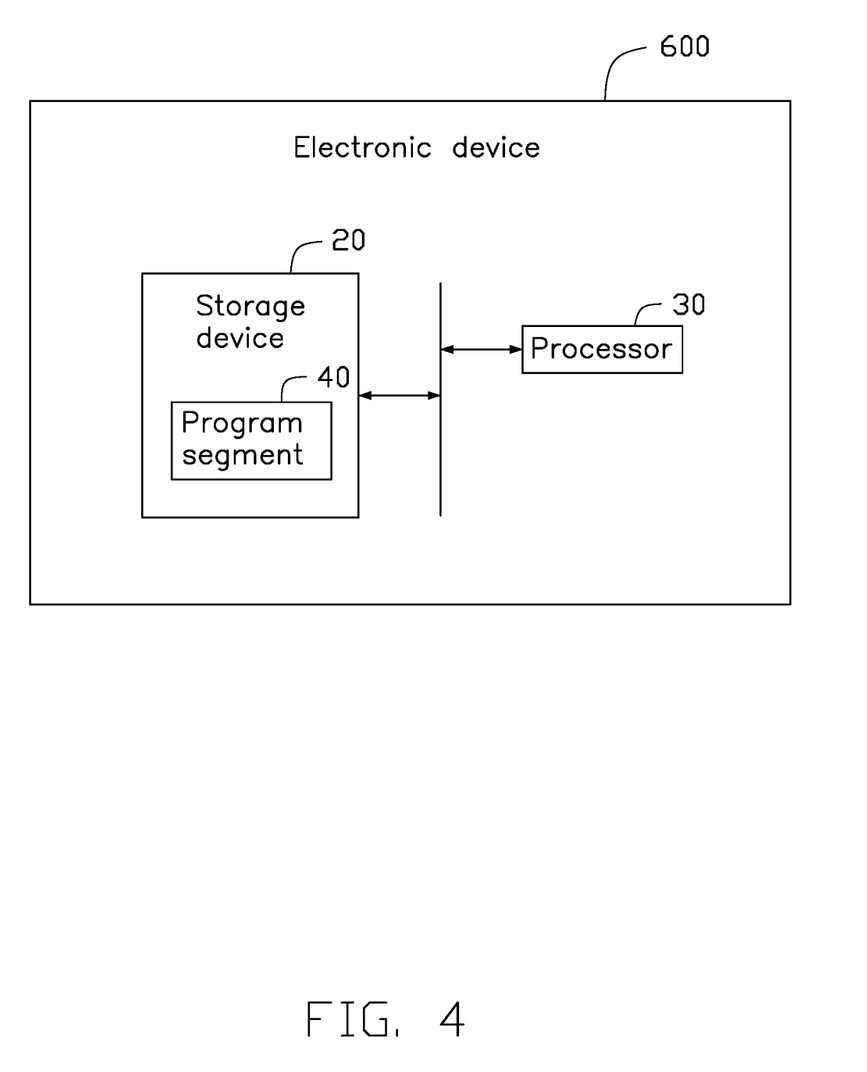
FIG. 4 is a schematic diagram of an electronic device according to an embodiment of the present disclosure.

In one embodiment, the method can be applied to an electronic device 600 (shown in FIG. 4). For an electronic device to detect a pneumonia area, the function for detecting provided by the method of the present disclosure can be directly integrated on the electronic device 600, or can be nm on the electronic device 600 in the form of a software development kit (SDK).

Each block shown in FIG. 3 represents one or more processes, methods, or subroutines, carried out in the example method. Furthermore, the illustrated order of blocks is illustrative only and the order of the blocks can change. Additional blocks can be added or fewer blocks may be utilized, without departing from the present disclosure. The example method can begin at block 31.

At block 31, obtaining a medical image.

In one embodiment, the medical image to be processed can be obtained through the information obtaining module 100. The function of the information obtaining module 100 is described in the paragraphs related to FIG. 1 and FIG. 2.

At block 32, processing the medical image to obtain a standard format image.

The embodiment of the present disclosure can process the medical image to obtain a standard format image through a preset image preprocessing method. In one embodiment, the medical image can be processed by the image preprocessing module 200 and the preset image preprocessing method to obtain the standard format image. The function of the image preprocessing module 200 is described in the paragraphs related to FIG. 1 and FIG. 2.

At block 33, obtaining a frame size of an initial pneumonia area.

In one embodiment, the frame size of the initial pneumonia area can be obtained by the information obtaining module 100. The frame size of the initial pneumonia area can be set according to an image size of the medical image. It can be understood that the frame size of the initial pneumonia area is smaller than the image size of the medical image. The function of the information obtaining module 100 is described in the paragraphs related to FIG. 1 and FIG. 2.

At block 34, processing the frame size of the initial pneumonia area through a preset algorithm and the standard format image, to obtain a frame size of a standard format pneumonia area.

In the embodiment, the frame size of the initial pneumonia area can be processed through the K-means clustering algorithm preset in the calculating module 300 and the standard format image, to obtain the frame size of the standard format pneumonia area. The function of the calculating module 300 is described in the paragraphs related to FIG. 1 and FIG. 2.

In the embodiment, feature extraction is performed on the standard format image to obtain a pneumonia area feature of the standard format image. An output pneumonia area is obtained by the frame size of the standard format pneumonia area and the pneumonia area features of the standard format image.

At block 35, inputting the standard format image and the frame size of the standard format pneumonia area to a pneumonia area detecting model to obtain an output pneumonia area.

In the embodiment of the present disclosure, the output pneumonia area can be obtained by the pneumonia area detecting model 400, the standard format image, and the frame size of the standard format pneumonia area. The function of the pneumonia area detecting model 400 is described in the paragraphs related to FIG. 1 and FIG. 2.

In the embodiment of the present disclosure, the method further includes optimizing the pneumonia area detecting model 400 through category weighting coefficient and FocalLoss loss function.

In the embodiment of the present disclosure, the model verifying module 500 can be used to obtain a standard pneumonia area, and verify the output pneumonia area and the standard pneumonia area to obtain the IOU between the output pneumonia area and the standard pneumonia area. If the IOU is greater than 0.5, the output pneumonia area is output. The function of the model verifying module 500 can be described in the paragraphs related to FIG. 2.

FIG. 4 illustrates an electronic device 600 in accordance with an embodiment of the present disclosure.

The electronic device 600 may include, but is not limited to, a storage device 20, at least one processor 30, and a program segment 40 stored in the storage device 20. The processor 30 may execute the program code of the program segment 40 to implement blocks 31-35 in the method shown in FIG. 3. The processor 30 may execute the program code of the program segment 40 to implement the functions of the pneumonia area detecting system 10 for detecting a pneumonia area shown in FIG. 1 and FIG. 2.

The modules 100-500 include computer instructions or codes in form of one or more programs that may be stored in the storage device 20, and which are executed by the at least one processor 30. In other embodiment, the modules 100-500 may also be a program instruction or firmware that is embedded in the processor 30.

The block diagram merely shows an example of the electronic device 600 and does not constitute a limitation to the electronic device 600. In other examples, more or less components than those illustrated may be included, or some components may be combined, or different components used. For example, the electronic device 600 may also include input and output devices, a network access devices, a bus, and the like.

The processor 30 may be a central processing unit (CPU), or may be another general purpose processor, a digital signal processor (DSP), an application specific integrated circuit (ASIC), a Field-Programmable gate array (FPGA) or other programmable logic device, a transistor logic device, a discrete hardware component. The general purpose processor may be a microprocessor. The processor 30 may also be any conventional processor. The processor 30 is a control center of the electronic device 100. The processor 30 connects the parts of the electronic device 600 by using various interfaces and lines.

The storage device 20 can be used to store the program segment 40. The processor 30 operates or executes the program segment 40 stored in the storage device 20 and recalls data stored in the storage device 20, and implements various functions of the electronic device 600. The storage device 20 may mainly include a storage program area and a storage data area, the storage program area may store an operating system, an application (such as sound playback and image playback) required for at least one function. The storage data area may store data created.

The storage device 20 may include a RAM, and may also include non-volatile memory such as a hard disk, a memory, a plug-in hard disk, a smart memory card (SMC), and a Secure Digital (SD) card, a flash card, at least one disk storage device, flash device, or other volatile or non-volatile solid-state storage device.

The modules and units integrated by the electronic device 600, if implemented in the form of software functional units and sold or used as separate products, may be stored in a computer readable storage medium. Based on such understanding, the present disclosure implements all or part of the processes in the foregoing embodiments, and the purposes of the disclosure may also be implemented and achieved by a computer program instructing related hardware. The computer program may be stored in a computer readable storage medium. The steps of the various method embodiments described above may be implemented by a computer program when executed by a processor. The computer program includes a computer program code, which may be in the form of source code, object code form, executable file, or some intermediate form.

The computer readable medium may include any entity or device capable of carrying the computer program code, a recording medium, a USB flash drive, a removable hard disk, a magnetic disk, an optical disk, a computer memory, a read-only memory (ROM), a random access memory (RAM), electrical carrier signals, telecommunications signals, and software distribution media.

Those of ordinary skill in the art should realize that the above embodiments are only used to illustrate the present disclosure, but not to limit the present disclosure. As long as they are within the essential spirit of the present disclosure, the above embodiments are appropriately made and changes fall within the scope of protection of the present disclosure.

What is claimed is:

1. A pneumonia area detecting method comprising:
    obtaining medical images;
    processing the medical images to obtain a standard format image;
    obtaining a frame size of an initial pneumonia area;
    processing the frame size of the initial pneumonia area through a preset algorithm and the standard format image, to obtain a frame size of a standard format pneumonia area; and
    inputting the standard format image and the frame size of the standard format pneumonia area to a pneumonia area detecting model, extracting features of the standard format image to obtain pneumonia area features of the standard format image, and obtaining an output pneumonia area through the frame size of the standard format pneumonia area and the pneumonia area features of the standard format image;
    wherein the pneumonia area detecting model detects the pneumonia area through a bidirectional feature pyramid network, the bidirectional feature pyramid network comprises a AdamW learning efficiency optimizer, and the AdamW learning efficiency optimizer learns features of the pneumonia area through weight decay.

2. The pneumonia area detecting method of claim 1, further comprising:
    calculating a size average value and a standard deviation of the medical images;
    outputting the standard format image according to the size average value and the standard deviation of the medical images.

3. The pneumonia area detecting method of claim 1, further comprising:
    optimizing the pneumonia area detecting model through a category weight coefficient and a loss function.

4. The pneumonia area detecting method of claim 1, further comprising:
    obtaining a standard pneumonia area; and
    verifying the output pneumonia area and the standard pneumonia area to obtain an intersection over union between the output pneumonia area and the standard pneumonia area.

5. The pneumonia area detecting method of claim 4, further comprising:
    outputting the output pneumonia area when the intersection over union is greater than a preset value.

6. A pneumonia area detecting system comprising:
    an information obtaining module obtaining medical images and a frame size of an initial pneumonia area;
    image preprocessing module processing the medical images to obtain a standard format image;
    a calculating module processing the frame size of the initial pneumonia area through a preset algorithm and the standard format image, to obtain a frame size of a standard format pneumonia area; and
    a pneumonia area detecting model obtaining an output pneumonia area according to the standard format image and the frame size of the standard format pneumonia area;
    wherein the pneumonia area detecting model is configurated to extract features of the standard format image to obtain pneumonia area features of the standard format image, and obtain the output pneumonia area through the frame size of the standard format pneumonia area and the pneumonia area features of the standard format image;
    wherein the pneumonia area detecting model detects the pneumonia area through a bidirectional feature pyramid network, the bidirectional feature pyramid network comprises a AdamW learning efficiency optimizer, and the AdamW learning efficiency optimizer learns features of the pneumonia area through weight decay.

7. The pneumonia area detecting system of claim 6, wherein the image preprocessing module is configured to calculate a size average value and a standard deviation of the medical images, and output the standard format image according to the size average value and the standard deviation of the medical images.

8. The pneumonia area detecting system of claim 6, wherein the calculating module is configured to optimize the pneumonia area detecting model through a category weight coefficient and a loss function.

9. The pneumonia area detecting system of claim 6, further comprising a model verifying module, the model verifying module obtaining a standard pneumonia area, verifying the output pneumonia area and the standard pneumonia area to obtain an intersection over union between the output pneumonia area and the standard pneumonia area.

10. The pneumonia area detecting system of claim 9, wherein the pneumonia area detecting model outputs the output pneumonia area when the intersection over union is greater than a preset value.

11. An electronic device, comprising:
a storage device; and
at least one processor, wherein the storage device stores one or more programs, when executed by the at least one processor, the one or more programs cause the at least one processor to:
obtain medical images and a frame size of an initial pneumonia area;
process the medical images to obtain a standard format image;
process the frame size of the initial pneumonia area through a preset algorithm and the standard format image, to obtain a frame size of a standard format pneumonia area; and
obtain an output pneumonia area according to the standard format image and the frame size of the standard format pneumonia area;
extract features of the standard format image to obtain pneumonia area features of the standard format image, and obtain the output pneumonia area through the frame size of the standard format pneumonia area and the pneumonia area features of the standard format image;
detect the pneumonia area through a bidirectional feature pyramid network, wherein the bidirectional feature pyramid network comprises a AdamW learning efficiency optimizer, and the AdamW learning efficiency optimizer learns features of the pneumonia area through weight decay.

12. The electronic device according to claim 11, wherein the at least one processor is further caused to:
calculate a size average value and a standard deviation of the medical images;
output the standard format image according to the size average value and the standard deviation of the medical images.

13. The electronic device according to claim 11, wherein the at least one processor is further caused to:
optimize a pneumonia area detecting model through a category weight coefficient and a loss function.

14. The electronic device according to claim 11, wherein the at least one processor is further caused to:
obtain a standard pneumonia area; and
verify the output pneumonia area and the standard pneumonia area to obtain an intersection over union between the output pneumonia area and the standard pneumonia area.

15. The electronic device according to claim 14, wherein the at least one processor is further caused to:
output the output pneumonia area when the intersection over union is greater than a preset value.

* * * * *